United States Patent
Lawandy

(10) Patent No.: US 7,760,421 B2
(45) Date of Patent: Jul. 20, 2010

(54) METHOD AND APPARATUS FOR ENHANCING PLASMON POLARITON AND PHONON POLARITON RESONANCE

(75) Inventor: Nabil M. Lawandy, Saunderstown, RI (US)

(73) Assignee: Solaris NanoSciences, Inc., Providence, RI (US)

( * ) Notice: Subject to any disclaimer, the term of this patent is extended or adjusted under 35 U.S.C. 154(b) by 504 days.

(21) Appl. No.: 11/716,183

(22) Filed: Mar. 9, 2007

(65) Prior Publication Data

US 2007/0273959 A1   Nov. 29, 2007

Related U.S. Application Data

(63) Continuation-in-part of application No. 11/100,339, filed on Apr. 6, 2005.

(60) Provisional application No. 60/780,746, filed on Mar. 9, 2006, provisional application No. 60/576,215, filed on Jun. 2, 2004, provisional application No. 60/565,754, filed on Apr. 27, 2004, provisional application No. 60/559,791, filed on Apr. 6, 2004.

(51) Int. Cl.
  *H01S 3/00* (2006.01)
(52) U.S. Cl. .................... 359/333; 359/341.5
(58) Field of Classification Search ............. 359/341.5, 359/333; 250/306; 422/82.05; 385/39; 436/164
  See application file for complete search history.

(56) References Cited

U.S. PATENT DOCUMENTS

| | | | |
|---|---|---|---|
| 5,864,397 A | 1/1999 | Vo-Dinh | |
| 6,408,123 B1 | 6/2002 | Kuroda et al. | |
| 6,424,418 B2 | 7/2002 | Kawabata et al. | |
| 6,539,156 B1 | 3/2003 | Dickson et al. | |
| 6,741,782 B2 | 5/2004 | Berini | |
| 6,782,179 B2 | 8/2004 | Bozhevolnyi et al. | |
| 6,861,263 B2 * | 3/2005 | Natan | 436/164 |
| 6,862,396 B2 | 3/2005 | Dickson et al. | |
| 7,043,134 B2 | 5/2006 | Berini et al. | |
| 7,110,154 B2 | 9/2006 | Ballato et al. | |
| 7,151,789 B2 | 12/2006 | Jette et al. | |
| 7,170,142 B2 | 1/2007 | Wojcik et al. | |

(Continued)

OTHER PUBLICATIONS

Bergman et al., "Surface Plasmon Amplification by Stimulated Emission of Radiation: Quantum Generation of Coherent Surface Plasmons in Nanosystems", Physical Review Letters, vol. 90, No. 2, pp. 027401-1-027401-4 (published Jan. 14, 2003).*

(Continued)

*Primary Examiner*—Mark Hellner
(74) *Attorney, Agent, or Firm*—K&L Gates LLP

(57) ABSTRACT

A metallic nano-particle surrounded by an amplifying medium results in a boundary condition that creates a singularity in the particle's dynamic polarizability at the localized surface plasmon resonance and at a critical value of the gain is disclosed. The boundary condition may be time dependent due to excitation by a sub-picosecond laser pulse and couples to the electromagnetic vacuum resulting in photon emission in an analogue of the Unruh Effect. The vacuum emission from 2-D nanostructures embedded in high gain laser dyes predicts energies nearly two orders of magnitude larger than the spontaneous emission background. The vacuum radiation is may have a unique dependence on the excitation.

2 Claims, 4 Drawing Sheets

U.S. PATENT DOCUMENTS

| | | | |
|---|---|---|---|
| 7,355,704 | B2 | 4/2008 | Lawandy |
| 2002/0048304 | A1 | 4/2002 | Barnes et al. |
| 2003/0059820 | A1 | 3/2003 | Vo-Dinh |
| 2003/0133681 | A1 | 7/2003 | Bozhevolnyi |
| 2003/0234978 | A1* | 12/2003 | Garito et al. ............ 359/341.5 |
| 2004/0150268 | A1* | 8/2004 | Garito et al. ................. 310/12 |
| 2004/0155184 | A1* | 8/2004 | Stockman et al. .......... 250/306 |
| 2005/0151973 | A1 | 7/2005 | Naya et al. |
| 2005/0239048 | A1 | 10/2005 | Lawandy |
| 2007/0253051 | A1 | 11/2007 | Ishihara et al. |
| 2007/0273959 | A1 | 11/2007 | Lawandy |

OTHER PUBLICATIONS

Hobson, et al., "Surface Plasmon mediated emission from organic light-emitting diodes," Advanced Materials, vol. 14, No. 19, pp. 1393-1396 (Oct. 2, 2002).

Barnes et al., "Surface plasmon subwavelength optics," Nature, vol. 424, pp. 824-830 (Aug. 14, 2003).

Citrin et al., "Plasmon-polariton transport in hybrid semiconductor-metal-nanoparticle structures with gain," Phys. Stat. Sol. (b) vol. 243, No. 10, pp. 2349-2353 (2006).

Maier, "Gain-assisted propagation of electromagnetic energy in subwavelength surface plasmon polariton gap waveguides," Optics Communications, vol. 258, pp. 295-299 (2006).

Citrin, "Plasmon-polariton transport in metal-nanoparticle chains embedded in a gain medium," Optics Letters, vol. 31, No. 1, pp. 98-100 (Jan. 1, 2006).

Nezhad et al., "Gain assisted propagation of surface plasmon polaritons on planar metallic waveguides," Optics Express, vol. 12, No. 17, pp. 4072-4079 (Aug. 23, 2004).

Jette-Charbonneau et al., "Bragg gratings based on long-range surface plasmon-polariton waveguides: comparison of theory and experiment," IEEE Journal of Quantum Electronics, vol. 41, No. 12, pp. 1480-1491 ( Dec. 2005).

Noginov et al., "Enhancement of surface plasmons in an Ag aggregate by optical gain in a dielectric medium," Optics Letters, vol. 31, No. 20, pp. 3022-3024 (Oct. 15, 2006).

Hooper et al., "Surface Plasmon Polaritons on thin-slab metal gratings," Physical Review B vol. 67, pp. 235404-1-7, (2003).

Steele et al., "Resonant and non-resonant generation and focusing of surface plasmons with circular gratings," Optics Express, vol. 14, No. 12, pp. 5664-5670 (Jun. 12, 2006).

Alencar et al., "Surface plasmon assisted directional laserlike emission from a highly scattering dye doped polymeric gain medium," Quantum Electronics and Laser Science Conference, vol. 57, pp. 173-174 (2001).

Lawandy, "Localized surface plasmon singularities in amplifying media," Applied Physics Letters AIP USA, vol. 85, No. 21, pp. 5040-5042 (Nov. 22, 2004).

Stockman et al., "Quantum nanoplasmonics: surface plasmon amplification by stimulated emission of radiation (SPASER)," Quantum Electronics and Laser Science, pp. 907-910 (2003).

Genov et al., "Resonant field enhancements from metal nanoparticle arrays," Nano Letters American Chem. Soc USA, vol. 4, No. 1, pp. 153-158 (2004).

Felidj et al., "Optimized surface-enhanced Raman scattering on gold nanoparticle arrays," Applied Physics Letters, vol. 82, No. 18, pp. 3095-3097 (May 5, 2003).

Xu et al., "Modeling the optical response of nanoparticle-based surface plasmon resonance sensors," Sensors and Actuators B vol. 87, pp. 244-249 (2002).

International Search Report for PCT/US2005/011727 mailed Nov. 7, 2005 (3 pgs.).

Written Opinion of the International Searching Authority for PCT/US2005/011727 mailed Nov. 7, 2005 (6 pgs.).

USPTO non-final Office action mailed Jan. 23, 2008 for U.S. Appl. No. 11/100,339 (6 pages).

USPTO non-final Office action mailed Dec. 24, 2008 for U.S. Appl. No. 11/100,339 (5 pages).

Response to non-final Office action dated Apr. 23, 2008 for U.S. Appl. No. 11/100,339 (6 pages).

Response to non-final Office action dated Apr. 24, 2009 for U.S. Appl. No. 11/100,339 (7 pages).

Berggren et al., "Stimulated emission and lasing in dye-doped organic thin films with Forster transfer," Appl. Phys. Lett., vol. 71, No. 16, pp. 2230-2232 (Oct. 20, 1997).

Berggren et al., "Organic solid-state lasers with imprinted gratings on plastics substrates," Appl. Phys. Lett., vol. 72, No. 4, pp. 410-411 (Jan. 26, 1998).

Kozlov et al., "Structures for organic diode lasers and optical properties of organic semiconductors under intense optical and electrical excitations," IEEE Journal of Quantum Electronics, vol. 36, No. 1, pp. 18-26 (Jan. 2000).

* cited by examiner

Figure 2. Absorption efficiency for a 20 nm core, 30 nm shell. Gain coefficient is (in cm$^{-1}$): a-0, b- $2.8 \cdot 10^4$, c-$3.9 \cdot 10^4$, d-$5.4 \cdot 10^4$.

METHOD AND APPARATUS FOR ENHANCING PLASMON POLARITON AND PHONON POLARITON RESONANCE

RELATED APPLICATIONS

This application is a Continuation-in-Part of U.S. patent application Ser. No. 11/100,339 filed Apr. 6, 2005 and entitled, "METHOD AND APPARATUS FOR ENHANCING PLASMON-POLARITON AND PHONON POLARITON RESONANCE," which claims benefit under 35 U.S.C. §119(e) to U.S. Provisional Application No. 60/559,791 filed Apr. 6, 2004, and entitled "PLASMON ENHANCEMENT BY AMPLIFYING MEDIA," and to U.S. Provisional Application No. 60/565,754 filed Apr. 27, 2004 and entitled, "PLASMON ENHANCEMENT BY ACTIVE MEDIA," and to U.S. Provisional Application No. 60/576,215 filed Jun. 2, 2004 and entitled, "LOCALIZED SURFACE PLASMON SINGULARITIES IN AMPLIFYING MEDIA," and claims the benefit under 35 U.S.C. §119(e) to U.S. Provisional Application No. 60/780,746 filed Mar. 9, 2006, and entitled "SCATTERING OF VACUUM STATES BY DYNAMIC PLASMON SINGULARITIES," the entire disclosures of each of which are hereby incorporated herein by reference for all purposes.

FIELD OF THE INVENTION

The invention relates to the field of optics, and more specifically to the field of generation and application of plasmon singularities and plasmon supporting structures.

BACKGROUND OF THE INVENTION

In 1974, Hawking predicted that a black hole can emit radiation with a temperature characteristic of its gravitational field strength at the event horizon. This process can be viewed as spontaneous vacuum pair production with the subsequent splitting of this pair at the event horizon by the gravitational field leaving the other to escape. The idea that primordial black holes could exhibit radiation with a characteristic temperature led to Unruh's subsequent prediction that an accelerated observer would experience a similar radiation with a temperature proportional to the proper acceleration. Unruh's result is both fundamental and intriguing as it opened up the possibilities of observing such vacuum related phenomena with accelerations generated in the laboratory. Subsequent work by Fulling and Davies showed that a single accelerated mirror rather than an observer can result in an altering of the energy density of vacuum leading to the emission of photons.

A related problem of transformations of vacuum fields was undertaken prior to both Hawking's black hole prediction and the work of Unruh and Davies by Moore who considered the problem of a quantized electromagnetic field in a dynamic cavity. Moore showed that photons can be created by the effect of moving cavity mirrors on the zero point field fluctuations. Following Moore's seminal work, a number of calculations related to the effects of rapidly changing boundary conditions on a massless field obeying a covariant wave equation followed. These efforts considered the cases of harmonically driven mirrors and also predicted photon creation from vacuum with various squeezing effects.

The importance of Unruh's work, coupled to the various treatments of electromagnetic vacuum with dynamic boundary conditions, has led to ideas on how to observe the general effect of photon creation from the vacuum state in the laboratory. In general, these proposals all focused on creating photons from highly accelerated particles or through non-adiabatic changes in boundary conditions that could lead to measurable signals. Unruh's seminal paper relates the observer temperature to the proper acceleration by:

$$T = \frac{ah}{ck} \tag{1}$$

where h is Plank's constant, c is the speed of light in vacuum, k is Boltzmann's constant and a is the proper acceleration. Based on equation (1), accelerations as large as $10^{23}$ m/s$^2$ only lead to temperatures comparable to those associated with the cosmic background radiation.

The first idea for observing the Unruh effect was due to Unruh himself who suggested using a hydrodynamic analogue of the Schwarzchild metric with a quantized phonon field [12]. This system had theoretical value beyond the suggested experimental measurements in that it provided a physical system to study the insensitivity of black hole evaporation on the exact form of the dispersion relations at high frequencies. However, the calculations showed that effective phonon temperatures of 1K required velocity gradients of 100 m/s per Angstrom, far beyond the capabilities of normal fluids.

Following Unruh's work on fluids, Bell and Leinaas suggested using the equilibration of electron spin polarization as a measure of the local proper frame temperature. In the case of linear accelerations, the time scale was glacial while for orbiting electrons the effect is highly complicated by orbital magnetic fields and the Sokolov-Ternov effect. Another effect relying on stored electrons was due to Rogers who suggested the use of a Penning trap coupled to a microwave cavity where photons emitted by the Unruh effect would lead to nonzero photon occupation numbers in certain cavity modes. This ingenious idea unfortunately predicts temperatures of 2-3K which are difficult to discern from stray mode coupling effects. Darbinyan et. al. proposed to use channeling phenomena in crystals to observe Unruh signals emanating from the scattering of vacuum by the transversely accelerated electrons. This proposal has the distinction of having the largest achievable accelerations with values as large as $10^{31}$ m/s$^2$ for the ultra-relativistic particles. Unfortunately, the process behind the emission, Compton scattering of vacuum photons, is swamped by the enormous Brehmsstrahlung radiation predicted by the Bethe-Heitler formula.

In 1989, Yablonovich proposed combining the accelerated mirror effect of Fulling and Davies with ultra-fast material response in semiconductors. Using a laser produced plasma front created though either real or virtual photoconductivity in semiconductors results in an effective acceleration of $10^{21}$ m/s$^2$ and an Unruh temperatures of ~4K. Calculations based on dynamic changes in dispersion relations estimated this type of dynamic Casimir effect version of the Unruh process could result in infrared emission powers of $10^{-9}$ W. These powers take place over timescales of less than a $10^{-12}$ s and therefore lead to emitted energies of a fraction of one infrared photon per experimental event. Again, the expected signals from the experimental scenario fall far from the requirements for measurable signals, proving the existence of the Unruh effect and connecting laboratory physics to processes occurring in black holes smaller than the size of an atom.

The most recent proposal for measuring the Unruh effect in the laboratory is due to Chen and Tajima who suggest taking advantage of ongoing developments in petawatt lasers to create violent electron accelerations as large as $10^{26}$ m/s$^2$. These types of accelerations are two orders of magnitude larger than those in plasma wakes and occur at the driving field frequencies as opposed to the slower natural modes of the plasma. This proposal predicts that petawatt lasers could result in Unruh energies which are four orders of magnitude weaker than the expected strong Larmor emission but with temporal and spatial signatures that are significantly different, allowing for detection. In addition, the authors suggest the possible use of coherent X-rays generated by free electron lasers to boost the signal to a value comparable to the Larmor energy. This approach has the highest acceleration values of any of the effects except for the channeling experiments of Darbinyan et. al. and does not suffer from Brehmsstrahlung radiation due to the interaction of charged particles with dense matter. Based on the combination of signal separation as well as overall background signal strengths, the proposal by Chen and Tajima remains the most promising approach to measuring the direct effect of acceleration of single electrons on the vacuum modes.

A plasmon is a density wave of charge carriers which form at the interface of a conductor and a dielectric. Plasmons determine, to a degree, the optical properties of conductors, such as metals. Plasmons at a surface can interact strongly with the photons of light, forming a polariton. Plasmon excitations at interfaces with dimensions comparable to or significantly smaller than the wavelength of excitation do not propagate and are localized. In ionic materials, phonons can produce a negative dielectric response and result in phonon-polaritons. Small scale dimensions lead to localized plasmon-polariton and phonon polaritons.

Localized surface plasmons have been observed since the time of the Romans, who used gold and silver nanoparticles to create colored glass objects such as the Lycurgus Cup (4th Century A.D.). A gold sol in the British museum, created by Michael Faraday in 1857, is still exhibiting its red color due to the plasmon resonance at ~530 nm. In more recent times, localized plasmons have been observed on rough surfaces and in engineered nanostructures and have led to the observation and exploitation of Surface Enhanced Raman Scattering (SERS) and new tunable plasmon structures with potential applications in biology and medicine.

Despite the large number of suggested schemes for observing the Unruh effect and the related non-adiabatic transformations of quantized electromagnetic vacuum modes, the process of popping a measurable number of photons out of the vacuum remains elusive to this day. This paper describes a novel electrodynamic system using localized surface plasmons embedded in amplifying media, which can result in subpicosecond bursts of photons being out of the vacuum with pulse energies two or more orders of magnitude above the background spontaneous emission in the same time interval.

SUMMARY OF THE INVENTION

In one aspect, the invention relates to a method for generating a plasmon-polariton or phonon-polariton resonance effect including: providing a structure capable of such resonance; providing a gain medium; and placing the structure in close juxtaposition to the gain medium. In one embodiment the structure is a nanoparticle. In another embodiment the structure is a nanostructure. In another embodiment the structure has a dimension D and the structure is placed within a distance less than or equal to D to the gain medium. In yet another embodiment the structure is placed within the gain medium or partially within the gain medium.

In yet another aspect the invention relates to a material for enhanced plasmon-polariton and phonon-polariton resonance. The material includes a gain medium; and a structure capable of plasmon-polariton or photon-polariton resonance positioned in close juxtaposition to the gain medium. In another embodiment the structure has a plasmon absorption curve, the gain medium has a gain curve and the peak of the plasmon absorption curve lies within the gain curve.

In still yet another embodiment the invention relates to a device for enhanced plasmon resonance. The device includes a gain medium; a structure capable of plasmon-polariton and phonon-polariton resonance positioned in close juxtaposition to the gain medium; and a device for stimulating such resonance in the structure.

Another embodiment of the invention includes a metallic nano-particle surrounded by an amplifying medium results in a boundary condition that creates a singularity in the particle's dynamic polarizability at the localized surface plasmon resonance and at a critical value of the gain. When this boundary condition is time dependent due to excitation by a sub-picosecond laser pulse, coupling to the electromagnetic vacuum results in photon emission in an analogue of the Unruh Effect. Estimates of the vacuum emission from 2-D nanostructures embedded in high gain laser dyes predict energies nearly two orders of magnitude larger than the spontaneous emission background. The vacuum radiation is predicted to have a unique dependence on the excitation, further distinguishing it from other radiative processes.

In yet another embodiment, a singularity in the optical polarizability of nanoscale metallic structures embedded in amplifying media is shown to create a dynamic boundary condition which strongly couples to the electromagnetic vacuum. The coupling of zero point vacuum energy to this transient and divergent response is predicted to emit radiation analogous to the Unruh effect which exceeds the spontaneous emission signal by nearly two orders of magnitude. An experimental system is described which can be used to observe this new radiation using available femtosecond lasers, gain media and nanofabricated structures is described. The basic effect described her can be utilized with other ordered plasmon supporting structures and with transient host boundary condition response that involves absorption or pure index of refraction changes, although it is expected that such media would have a weaker emission due to the lack of a singularity as described for the case of gain.

Another embodiment includes a plasmon supporting structure in a surrounding medium which changes its optical properties rapidly in time as a generator of radiation is disclosed herein. The surrounding medium can change its absorption/gain properties or simply its index of refraction or both. This can be accomplished through mechanical, electrical, thermal or optical means. The composite material created from a plurality of such plasmons supporting structures in a host is also disclosed.

BRIEF DESCRIPTION OF THE DRAWINGS

These and other aspects of the invention will be better understood by reference to the specification and drawings in which.

DETAILED DESCRIPTION

Figure 1:
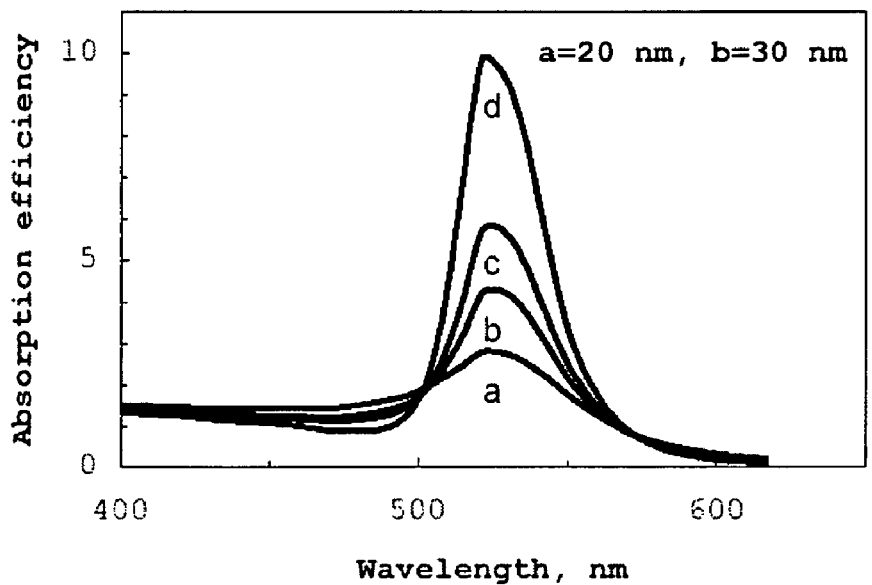
FIG. 1 is a diagram of the maximum internal and surface field as a function of β for various incident field values.

The invention will be more completely understood through the following detailed description, which should be read in conjunction with the attached drawings. Detailed embodiments of the invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the invention in virtually any appropriately detailed embodiment.

The invention herein relates to the use of the localized surface plasmon-polariton resonance on a surface in the presence of a gain medium. In one embodiment the surface is on a nanostructure that exhibits a greatly enhanced magnitude when the surrounding gain medium has gain near a critical value. In one embodiment this combination leads to large enhancements of the plasmon-polariton resonance even when the gain of the medium is saturated. Such a gain medium will exhibit strong scattering within the plasmon band leading to low threshold random laser light generation and light localization effects. The localization effect will greatly increase Surface Enhanced Raman Scattering signals for rapid single molecule detection, identification and sequencing.

Beyond the well studied single structure resonances is the response of clusters and aggregates. It has been shown theoretically and experimentally that homogenous aggregates of structures supporting localized surface plasmon-polariton resonances can lead to extremely large enhancement of local field amplitudes exceeding those of single structures. Of particular interest are "fractal" metal nanoparticle aggregates, which when combined with resonant microcavities have led to plasmon-polariton enhancements of the order of $10^{11}$. Devices based on this effect are currently under development as ultra-sensitive gas and biological sensors.

Certain embodiments disclosed herein relate to the response of structures that support localized surface plasmon-polariton and phonon-polariton resonances when the surrounding medium is optically active. Specifically, it is shown that in the long wavelength or DC limit of the Maxwell Equations, at a critical value of amplification, in even the simplest of systems, a single metallic nanoparticle in a semi-infinite gain medium exhibits a singularity. This singularity, which is suppressed in a full multiple treatment using Mie theory, results in a substantially infinite internal field, surface field and scattering cross-section for the nanoparticle. In the presence of saturation, this mathematical singularity is suppressed, but still exhibits local fields that are much higher than those in conventional plasmon resonance, when the critical level of unsaturated gain is exceeded. In the exact Mie solution, the fields can be several orders of magnitude higher than the case without gain and will also result in gain saturation in the medium within a few radii of the structure.

In more detail, for the case of a metallic spherical particle of radius $R_o \ll \lambda$, and a complex relative dielectric constant $\in_1(\omega)$, surrounded by an infinite medium with a complex relative dielectric constant $\in_2(\omega)$, the field inside the particle in the long wavelength limit of the theory is given by:

$$E = E_0 \left( \frac{\varepsilon_2 - \varepsilon_1}{\varepsilon_1 + 2\varepsilon_2} \right) \quad (2)$$

where $\omega$ and $E_0$ are the frequency and vector amplitude of the linearly polarized incoming plane wave.

For simple metals, $\in_1(\omega)$ can be approximated by the well accepted Drude response given by:

$$\in_1(\omega) = 1 + \chi_1'(\omega) + i\chi_1''(\omega) \quad (3)$$

where $$\chi_1'(\omega) = \frac{-\omega_p^2}{\omega^2 + \gamma^2} \quad (4a)$$

and $$\chi_1''(\omega) = \frac{-\gamma \omega_p^2}{\omega^3 \left(1 + \frac{\gamma^2}{\omega^2}\right)} \quad (4b)$$

$\omega_p$ is the plasma frequency of the metal and $\gamma$ is the electron momentum dephasing rate which is typically two orders of magnitude smaller than $\omega_p$ at room temperature. In the limit of $\gamma^2/\omega^2 \ll 1$, the susceptibilities for the metal are given by:

$$\chi_1'(\omega) = \frac{-\omega_p^2}{\omega^2} \quad (5a)$$

and $$\chi_1''(\omega) = \frac{-\gamma \omega_p^2}{\omega^3} \quad (5b)$$

Use of Eqs. (3) and (5a) in Eq. (2) results in:

$$\frac{\varepsilon_2 - \varepsilon_1}{\varepsilon_1 + 2\varepsilon_2} = \frac{\varepsilon_2 - 1 + \frac{\omega_p^2}{\omega^2} - i\chi_1''}{2\varepsilon_2 + 1 - \frac{\omega_p^2}{\omega^2} + i\chi_1''} \quad (6)$$

The metallic particle plasmon resonance occurs when the real part of the denominator in Eq. (6) equals zero. From previous work, with the $\in_2(\omega)$ assumed to have a vanishingly small absorption or gain, the resonance occurs at:

$$\omega_0^2 = \frac{\omega_p^2}{2\varepsilon_2 + 1} \quad (7)$$

This leads to a field enhancement within the particle given by:

$$E = E_0 \left[ \frac{3i\varepsilon_2 \omega_p}{(2\varepsilon_2+1)^{\frac{3}{2}} \gamma} - 1 \right] \quad (8)$$

Equation (8) reflects the enhancement of the internal and external local fields surrounding the particle that lead to the absorption of metallic colloids and effects such as SERS. Typical values of $\varepsilon_2 \sim 1$ give field enhancements of $\sim 10^2$.

Of particular interest is when this enhancement is not limited by the incomplete vanishing of the denominator in Eq. (6). The presence of a strongly amplifying response in $\varepsilon_2$, can cause such a complete cancellation in the absence of saturation. The entire denominator in Eq. (6) can equal zero when both the real and the imaginary parts vanish simultaneously. To determine the conditions under which this occurs, the external medium ($\varepsilon_2$) response is modeled by:

$$\varepsilon_2(\omega) = \varepsilon_2'(\omega) + i\varepsilon_2''(\omega) \quad (9)$$

where $\varepsilon_2'(\omega)$ is the real part of the dielectric response commonly used to determine the resonance in Eq. (6) and $\varepsilon_2''(\omega)$ includes all absorptive or amplifying responses of the surrounding medium.

The inclusion of an amplifying response in the medium surrounding the metal particle results in an internal field at plasmon resonance given by:

$$E = \frac{E_0}{\beta+1} \left[ \left( \frac{\beta}{2} - 1 \right) + \frac{3i\varepsilon_2'}{\chi_1''(\omega_0)} \right] \quad (10)$$

where $$\beta = \frac{2\varepsilon_2''(\omega_0)}{\chi_1''(\omega_0)}.$$

Comparing the real and imaginary parts of Eq. (10) for typical values of the parameters shows that E is dominated by the imaginary or out of phase response and complete cancellation of the denominator in Eq. (9) in the limit $$\frac{\gamma}{\omega_0} \ll 1$$

results in a field singularity when $\beta+1$ approaches zero. This singularity occurs due to the cancellation of the dissipative force in the Drude model by an opposite force arising from the bound surface charge at the interface of the gain medium and the metal surface. Similar results can be obtained using the actual experimentally measured dielectric functions for the metal or plasmon-polariton material.

Modeling $\varepsilon_2''$ by a single symmetric gain line susceptibility, $\chi_2''(\omega)$ centered at $\omega_0$ yields the condition for plasmon singularity given by:

$$\chi_2''(\omega_0) = \frac{\gamma}{2\omega_p} (2\varepsilon_2' + 1)^{\frac{3}{2}} \quad (11)$$

where the facts that $\chi_1'(\omega_0) = 0$ and $\varepsilon_2'(\omega)$ is determined by only the host properties are assumed. Using the relationship between the intensity gain coefficient, $\alpha(\omega)$, the wave vector in surrounding medium and $\chi_1''(\omega)$, the critical value of the resonant gain in the surrounding medium at which the plasmon singularity occurs, is calculated:

$$\alpha_c(\omega_0) = \frac{(2n_1^2(\omega_0)+1)\gamma}{2cn_1(\omega_0)} \quad (12)$$

where $n_1^2(\omega_0) = \varepsilon_1'(\omega_0)$ and c is the speed of light. Using $n_1 = 1.3$ and accepted $\gamma$ values for silver and gold, $\alpha_c \cong 1.5 \times 10^3$ cm$^{-1}$ and $\alpha_c \cong 2.25 \times 10^3$ cm$^{-1}$ respectively. This magnitude of gain is attainable using dyes and semiconductor materials and structures as gain media. Using a value of $\sigma_e = 2.5 \times 10^{-16}$ cm$^2$ as a typical linecenter emission cross-section for laser dyes, the critical dye density of $$\rho_c = \frac{\alpha_c}{\sigma_a} = 6.0 \times 10^{18} \text{ cm}^{-3} \text{ or a } 10^{-2}$$

molar concentration. The critical gain required can be lowered significantly by the use of nanorods where interband damping is suppressed. Recent experiments on Au nanorods indicate that at least an order of magnitude reduction in $\alpha_c$ can be achieved in such systems.

For the plasmon singularity in silver at ~420 nm, the divergence of the field within and outside the particle will be countered by the saturation of the surrounding medium. Using a two level model for the amplifying response of the surrounding medium in the rate equation limit, $\beta$ is expressed as a function of the field ($\vec{E}$) outside the particle:

$$\beta(\vec{E}) = \frac{\beta}{1 + \frac{|\vec{E}|^2}{E_s^2}} \quad (13)$$

where $E_s$ is the saturation electric field related to the saturation intensity of the transition through the Einstein B coefficient and the relaxation rate. Since $\vec{E}$ is a function of the radial and angular coordinates, the exact self consistent solution must be solved beginning with the boundary conditions reflecting a spatial variation in $\varepsilon_2$. However, since it is the values of $\varepsilon_2$ at the boundary or surface that provide the restoring forces that drive the plasmon resonance, the estimate of $|\vec{E}| \sim E$, the internal field and the maximum value at the surface when the incident field $E_0$ is small.

The complex dielectric function of the particle's surrounding, obtained by means of introduction of gain, transfers the normally complex natural frequencies of the sphere into the real domain, and thus makes it possible to increase local field intensities by as much as an order of magnitude, compared with those obtained near surface plasmon resonance of metal nanoparticles in non-amplifying media. These ideas are further developed in a rigorous manner as a generalized Mie solution for absorption of a coated gold nanosphere, utilizing numerical algorithms for evaluation of Bessel-Riccati functions and their derivatives. FIG. 1 shows the absorption efficiency for a 20 nm core, 30 nm shell including finite particle effects.

The field enhancement is mirrored by a gigantic increase in scattering cross-section. The ratio of the enhanced cross-section to the conventional plasmon resonance cross-section is arbitrarily large for arbitrarily small driving fields since the final field is locked at a value near $E_s$. Such a large enhancement in the presence of gain is expected to result in random laser action and light localization phenomena at exceedingly low concentrations of scattering particles. Furthermore, such a medium, unlike previous systems using high index of refraction particles such as $TiO_2$ and ZnO, would be transparent at all wavelengths outside the absorption bands of the gain medium.

Figure 2:
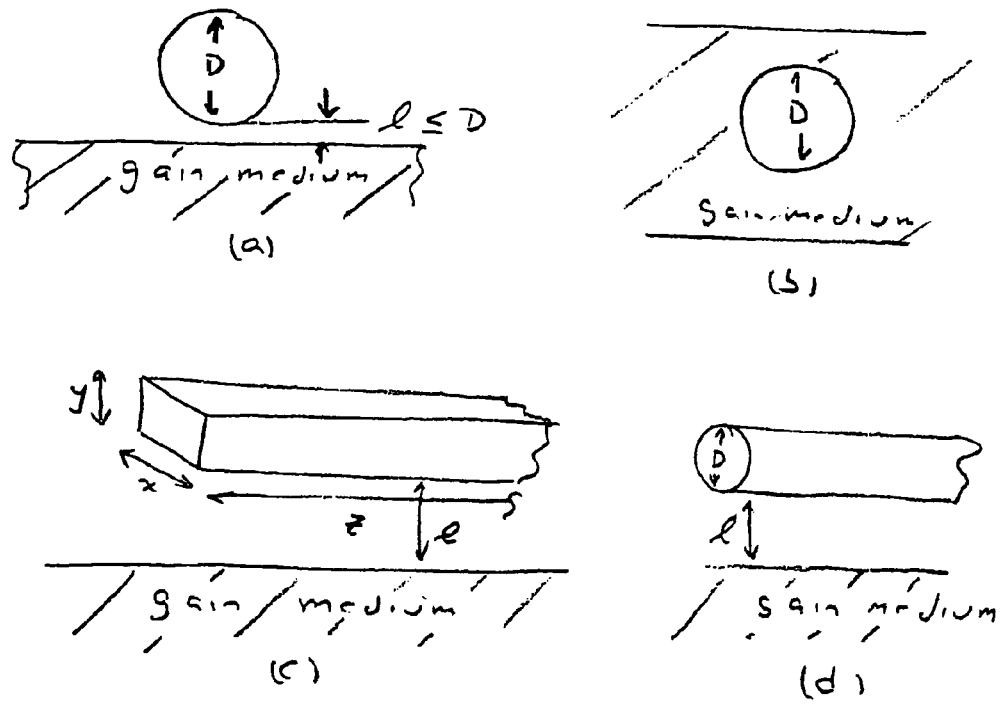
FIGS. 2 a-d are various embodiments of the invention.

Referring to FIGS. 2 a-d, multiple embodiments of the invention constructed in accordance with the above principles include (FIG. 2a) a spherical particle or shell of plasmon resonant material of diameter D (<<the wavelength of light $\lambda$) positioned a distance $1 \leq D$ from the surface of the gain medium; (FIG. 2b) the particle or sphere of FIG. 2a immersed in the gain medium; (FIG. 2c) a rod of plasmon resonant material having dimensions x,y,z, where x, and/or y and/or z are << the wavelength of light $\lambda$ and (FIG. 2d) of a cylinder of diameter D (<<the wavelength of light $\lambda$) positioned a distance $1 \leq D$ from the surface of the gain medium. The plasmon resonant material in one embodiment is a metal, for example silver or gold. In another embodiment the plasmon resonant material is an ionic crystal. In one embodiment the gain medium is a high gain laser dye such as rhodamine or coumarin which is optically or electrically pumped to excite the medium.

Figure 3:
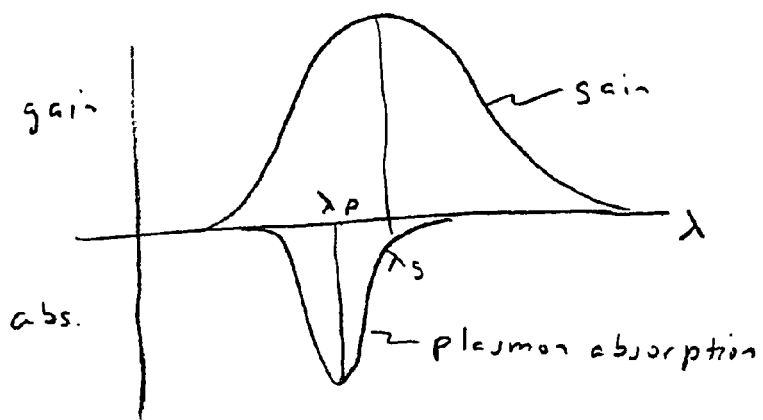
FIG. 3 is a depiction of a gain curve for the gain medium and the absorption curve for a plasmon resonant material.

Referring to FIG. 3, the gain curve for the gain medium and the plasmon absorption curve of the plasmon material are depicted. The plasmon material and the gain medium are selected so that the plasmon absorption curve peak falls within the gain curve of the medium.

An application of this new material system is the further enhancement of Surface Enhanced Raman Scattering (SERS). The SERS mechanism relies on both the local field enhancement around the metal particles as well as the chemical coupling of the molecules to the metallic electronic response. Typically this latter chemical enhancement factor is of the order of $10^2$. Using standard SERS and based on this factor, as well as the local field enhancement, single molecule detection of adenosine on colloidal silver clusters was achieved with 100 mW of laser power and a 1 s integration time. Similarly, the SERS spectrum of a single hemoglobin molecule was recorded with 20 μW of power and a 200 s measurement time.

Use of the SERS technique in the presence of a gain medium which has an unsaturated gain exceeding the critical value could result in measurements with greatly reduced laser powers and times. For example, the measurement of hemoglobin on particles of gold or silver could be performed with picowatts of power. Further combination of SERS in the presence of critical gain with shape engineered and core-shell plasmon resonances can lead to tunability of the effect from the visible to the IR. This modification to SERS could potentially lead to a new class of ultra-sensitive and compact molecular detection, identification and sequencing instruments for biological, medical and genomics applications and potentially provide the necessary sensitivity to eliminate the need for PCR amplification.

Another application of the material of the invention is as a low threshold coherent emitter. In this case the combination of gain medium and plasmon resonant particles causes coherent radiation to be emitted from the material without the use of a cavity.

In still yet another embodiment an array of projects of plasmon resonant material is placed in close juxtaposition to, in or partially in a gain medium, with each of the projections having a height D less than or equal to the wavelength of light that will cause the plasmon resonant effect.

Figure 4:
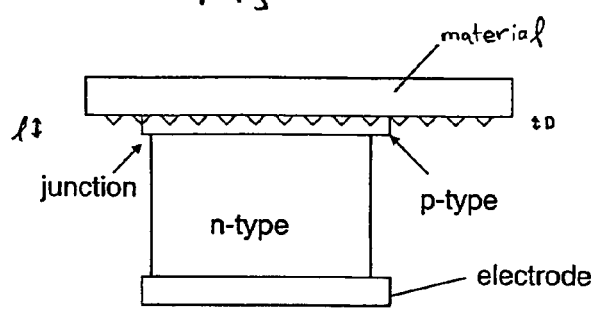
FIG. 4 is a diagram showing a plasmon resonant material having a roughened surface placed in close juxtaposition to a P-N semiconductor junction forming an electrode.

In still yet another embodiment the plasmon resonant material is placed in close juxtaposition to the gain junction of a laser diode. In still yet another embodiment the plasmon resonant material having a roughened surface placed in close juxtaposition to a P-N semiconductor junction, forming an electrode. As shown in FIG. 4, plasmon resonant material having a roughened surface with a dimension D (<<the wavelength of light $\lambda$) is positioned a distance $1 \leq D$ from the P-N junction.

Another embodiment of the present invention includes plasmon singularities in amplifying media. A metallic nanoparticle whose dimensions are significantly smaller than the wavelength of light, embedded in a medium capable of amplification. The presence of an amplifying medium at the particle boundary can create a singularity in the dynamic polarizability of the particle. This singularity arises from the possibility of completely cancelling out both the real and imaginary parts of the denominator in the particle polarizability expression when there is an amplifying medium outside of the particle and at its boundary. In the case of the exact Mie solutions, this corresponds to the situation where the entire denominator of the $B_n$ coefficient (n=1) vanishes.

In the static limit of the equations, where the particle is a spheroid whose dimensions are small compared to the wavelengths of interest, all size dependence is lost, and these divergent solutions occur when:

$$Re[\epsilon_1(\omega_0)] = p_i Re[\epsilon_2(\omega_0)] \tag{14a}$$

$$Im[\epsilon_1(\omega_0)] = p_i Im[\epsilon_2(\omega_0)] \tag{14b}$$

Where $\epsilon_1(\omega_0)$ and $\epsilon_2(\omega_0)$ are the complex dielectric constants of the metal and the surrounding gain medium, $\omega_0$ is the frequency of the solution, and $p_i$ is a parameter describing the effects of particle asymmetry. As can be seen from equations (14a) and (14b), oblate and prolate particles shift the resonances and the magnitudes required to achieve these conditions simultaneously. Although the exact frequencies of the singularities depend on the particle size through dynamic corrections as well as radiative damping terms, this set of equations very accurately locates and predicts the The dielectric functions of the metal and the surrounding medium along with the asymmetry parameter for spheroids can be used to formulate the factor, g, which accounts for much of the electromagnetic enhancement in Surface Enhanced Raman Scattering (SERS). The parameter g can be used to express the polarizability along the $i^{th}$ axis of the particle and is given by:

$$g = \frac{\varepsilon_1(\omega) - \varepsilon_2(\omega)}{\varepsilon_1(\omega) - p_i \varepsilon_2(\omega)} \tag{15}$$

where $p_i$ is related to the aspect ratio of the particle and assumes the value $p_i=2$ for a sphere.behavior for small particles.

Figure 5:
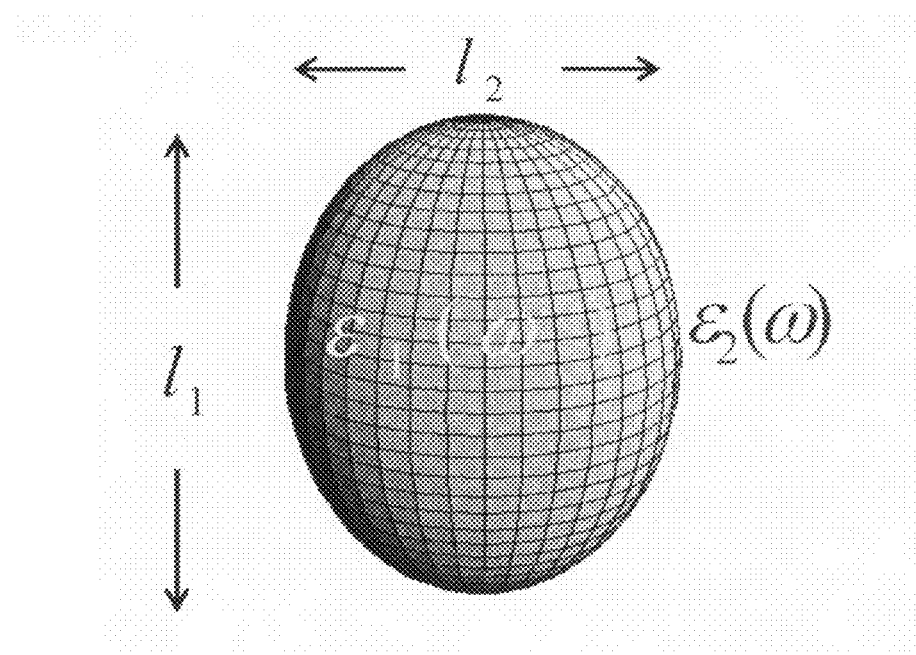
FIG. 5 is a metallic nano-particle spheroid, in accordance with an embodiment of the present invention, with major and minor axis lengths of $l_1$ and $l_2$ respectively.

The frequency response of the system can be simplified using a form of $\epsilon_2(\omega)$ which is given by the sum of a transparent background medium with a real dielectric function $\epsilon_2'(\omega)$ and a gain with a symmetric lineshape $G(\omega)$ which is relatively narrow in comparison to the variations of the metal dielectric functions. Using this approximation, we can decouple the magnitude of the gain from frequency of the singularity conditions in g by placing the gain linecenter at $\omega_0$ where there is no contribution to the real part of the dielectric properties due to this resonance. With this form for $\epsilon_1(\omega)$, we are able to formulate the dynamic polarizability of the metal particle in a gain medium along a particular particle axis and at the plasmon resonance. Turning now to FIG. 5, a metallic nano-particle spheroid with major and minor axis lengths of $l_1$ and $l_2$ respectively is shown. The complex dielectric constant of the particle is $\in_1(\omega)$ while that of the external amplifying medium is $\in_2(\omega)$. The polarizability of the spheroid $\alpha_1$ at $\omega_0$ along the major axis is given by:

$$\alpha_1 = \frac{4\pi i(l_1 l_2^2)(p_1+1)}{3}\left[\frac{g_0 \text{Im}(\varepsilon_1) + p_1\psi\alpha_g}{\text{Im}(\varepsilon_1) - p_1\psi\alpha_g}\right] \quad (16)$$

Where $g_0$ is the value of g for the case where $\text{Im}(\in_2)=0$, $\alpha_g$ is the peak gain in medium 2 and is centered at $$\omega_0, n_2^2 = \varepsilon_2', \psi = \frac{cn_2}{4}\frac{\Delta\omega}{\omega_0}G(\omega),$$

$\Delta\omega$ is the gain linewidth and $$p_i = \frac{1-L_i}{L_i}.$$

The factor $L_i$ which assumes the value of $$L_i = \frac{1}{3}$$

for a sphere is given by:

$$L_1 = \frac{1-e^2}{e^2}\left\{\frac{1}{2e}\ln\left(\frac{1+e}{1-e}\right)-1\right\} \quad (17)$$

where $$e^2 = 1-\left(\frac{l_2}{l_1}\right)^2.$$

The polarizability will exhibit a singularity when the gain in the medium surrounding the particle reaches a specific value determined by the imaginary part of the metal's dielectric response. This singularity and its mathematical behaviour near the critical gain value exist in the full Mie scattering theory and are very well approximated by the results given here for particles small compared to the wavelength. Equation (16) for the polarizability of a spheroid along its major axis can be well approximated by neglecting the $p_1\psi\alpha_g$ term in the numerator since $g_0 \Box 1$ as confirmed by calculations and SERS experiments. This simplification allows us to express the polarizability $\alpha_1$ in the case of a surrounding medium with a peak gain $\alpha_g$ at or near $\omega_0$ by:

$$\alpha_1 = \frac{4\pi i(l_1 l_2^2)(p_1+1)g_0}{3\left(1-\frac{\alpha_g}{\alpha_s}\right)} \quad (18)$$

$\alpha_s$ is the critical gain value required to produce a singularity and is given by:

$$\alpha_s = \frac{\text{Im}[\varepsilon_1(\omega_0)]}{p_1\psi} \quad (19)$$

When the gain in the surrounding medium is switched on rapidly, the polarizability of the particle becomes time dependant and can be arbitrarily close to a divergence. The frequency dependence of $\alpha_1$ remains valid as long as excitations of the gain with time characteristics slow compared to $\omega_0$ are considered. For typical metals, the frequency of the plasmon is approximately $10^{15}$ s$^{-1}$ making this approximation valid for gain dynamics on time scales of $10^{-13}$ s-$10^{-12}$ s.

The estimates of the critical gain that results in a singularity in the dynamic polarizability have neglected the sometimes observed quenching of fluorescence at or near metallic surfaces. This quenching often takes place over a distance of up to 10 nm from the metal, which in our model system would imply a shell of passive response separating the gain medium and the metal surface. Analysis of this situation in the case of a sphere of radius $R_0$ and in the electrostatic limit, shows that a shell of quenched gain will not suppress the radiation predicted. Specifically it can be shown that if a shell of thickness $\delta \ll R_0$ separates the metal and the gain medium, the dominant effect is to shift the plasmon frequency and to increase the required gain ($\alpha_s$) at which the singularity occurs. The gain required is approximately given by:

$$\alpha_s(\delta) = \frac{\alpha_s}{1-\frac{6\delta}{R_0}} \quad (20)$$

Estimating this using $R_0 \sim 100$ nm and $\delta=10$ nm, we find that the required gain to achieve a singularity is increased by a factor of 2.5, still within the range of available gain media as discussed later in the paper.

One embodiment of the invention includes vacuum emission of photons. Rapidly increasing or decreasing the gain in the surrounding medium results in a dynamic boundary condition analogous to the optical cavity with moving mirrors and results in photons generated from the vacuum state. The radiated power can be estimated from the acceleration of the internal electron coordinate and the well know expression for the radiation terms of a dipole:

$$P = \frac{[\ddot{\mu}]^2}{12\pi\varepsilon c^3} \quad (21)$$

Where $\mu$ is the dipole moment of the particle and is given by the product of the polarizability and the driving field, $E_\omega(t)$ and $\ddot{\mu}$ is the second derivative in time of this induced dipole. The driving field $E_\omega(t)$ is taken to arise from the zero point energy of the vacuum state of the electromagnetic field in a parallel to the well known relationship between spontaneous emission and stimulated emission.

Describing the denominator of the polarizability expression in equation (20) by a function $\beta(t)$, retaining only terms which depend on only the second derivative of the polarizability, and using the well known expression for the polarization specific density of states of the electromagnetic field, we arrive at the radiated power per unit frequency of photons from vacuum:

$$P = \frac{32\pi^2 n_2^6 (l_1^2 l_2^4)(p_1+1)^2 g_0^2 \hbar \omega^3}{27 c^6} \left\{ \frac{2(\dot{\beta})^2}{\beta^3} - \frac{\ddot{\beta}}{\beta^2} \right\}^2 \quad (22)$$

The energy per particle of emitted photons is given by the time integral of the power expression and the details of the dynamics of the gain as described through $\beta(t)$.

Figure 6:
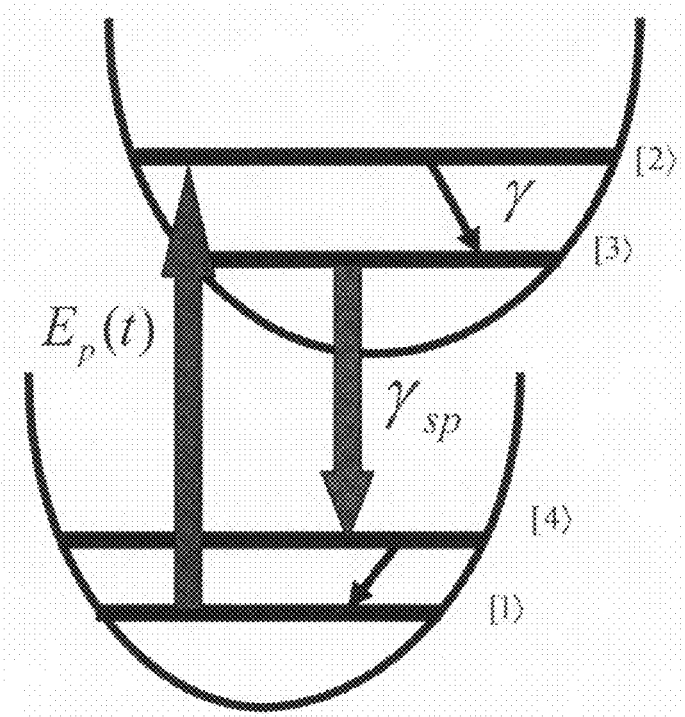
FIG. 6 is a four level model describing the excitation and relaxation dynamics of the dye molecules which provide the ultra-fast gain boundary condition on the plasmon supporting particles is shown in accordance with an embodiment of the present invention.

Another embodiment of the invention includes an experimental system for observing the vacuum photon emissions. A viable system to observe this effect is comprised of metallic spheroids or rods embedded in a transparent solvent containing high gain dyes, semiconducting polymers or quantum dots to provide an adjustable source of gain. The time dependence of the gain for dyes can be determined through the use of well established models for such large molecules in a solvent bath. Models for laser dyes such as the xanthenes and others have been confirmed experimentally and time constants have been established using picosecond and femtosecond spectroscopic techniques. FIG. 6 shows a four level model for a dye molecule where levels [1> and [4> are vibronic levels in the ground singlet state and [2> and [3> are in the excited singlet state. In this simple model, a population inversion takes place between levels [3> and [4>. The relaxation between vibronic levels within the same electronic state is due to a combination of coupling to internal modes due to anharmonicity and to the solvent molecules. These processes have time scales of $10^{-14}$ s and $10^{-13}$ s-$10^{-12}$ s respectively.

Turning now to FIG. 6, a four level model describing the excitation and relaxation dynamics of the dye molecules which provide the ultra-fast gain boundary condition on the plasmon supporting particles is shown. The blue arrows indicate excitation of the upper singlet in under 100 femtoseconds and the red arrows indicate the vacuum and spontaneous emission and gain transition.

In the limit of a pump pulse ([1>→[2>) of duration, $T_p << \gamma^{-1}$, a population inversion and gain develop on two time scales associated with the upper level being either [2> or [3>. In most dyes, the strongest transitions and source of gain are the ones with an upper level near the bottom of the excited singlet state. Using this limit for the gain and assuming a delta function excitation as the pump, we have a gain build-up driven by the internal relaxation process and hence the population dynamics of level [3> since level [4> is initially depopulated. The time dependent population of level [3> after the pump pulse is given by:

$$N_3(t) = N_{10} B_{12} E_p (e^{-\gamma_{sp} t} - e^{-\gamma t}) \quad (23)$$

where $\gamma_{sp}$ is the decay rate of level [3> which is dominated by spontaneous emission.

$N_{10}$ is the ground state population density at equilibrium, $B_{12}$ is the Einstein coefficient at the pump wavelength and $E_p$ is the pump pulse fluence. Combining this result with the peak emission cross section of the dye, $\sigma_{34}$, leads to an expression for $\beta$ (t) in the limit of $\gamma_{sp} << \gamma$ condition typical of high gain media such as dyes:

$$\beta(t) = \eta(1 + \kappa e^{-\gamma t}) \quad (24)$$

where $$\xi = \frac{N_{10} B_{12} E_p \sigma_{34} p_1 c n_2}{\omega_0 \text{Im}[\varepsilon_1(\omega_0)]}, \eta = 1 - \xi \text{ and } \kappa = \frac{\xi}{1-\xi}.$$

Substitution of this form of $\beta$ (t) into the power expression and integrating over time leads to the energy emitted per particle, per event. The integration limits are T=0 to $T_0$ and $\delta\omega$ is the bandwidth of interest. In the case that the time considered is such that $\kappa e^{-\gamma T_0} <<1$ and $\kappa <<1$, the energy emitted is given by:

$$E = \frac{32\pi^2 n_2^6 (l_1^2 l_2^4)(p_1+1)^2 g_0^2 \hbar \omega^3 (\delta\omega) \gamma^3}{810 c^6 (1-\xi)^2} \quad (25)$$

The energy expression for the emitted photons is a result of the dynamic acceleration term in only the polarizability since all other terms and cross terms in the full expression $\mu$ result in phase effects and no energy exchange. An evaluation of the emitted energy can be made using available data on laser dyes and the metal particle dielectric functions. Choosing a silver spheroid of length $l_1$=350 nm and an aspect ratio of ~5 ($p_1$=19) results in $\omega_0$=2.2×10$^{15}$ s$^{-1}$ (850 nm), a critical value of the gain $\alpha_s$=536 cm$^{-1}$ and a value of $g_0$~10$^2$. Amplification at or very near the plasmon resonance can be achieved using pulsed laser pumping of the first singlet state in several high gain dyes including DTTCI, DNTTCI, HITCI Styryl 9M and Styryl 15 in solvents such as DMSO, ethanol and methanol. By choosing the proper solvent or mixture of solvents, the dye linecenter emission can be positioned on or very close to $\omega_0$.

The singularity factor $\xi$ can be determined and controlled through a combination of the pump fluence and the concentration of dye molecules in the solution. Choosing a value of $\xi$=0.99, a dye bandwidth of ~150 nm and determining $\delta\omega$, from the condition that the overall energy drop to one half its peak value when the frequency if the emission is detuned from the exact singularity position, results in $\delta\omega$=5×10$^{13}$ s$^{-1}$. Inserting all of these parameters with $n_2$=1.3 and $\gamma$=1×10$^{13}$ s$^{-1}$ into equation (24), we predict an energy of ~1.8×10$^{-17}$ J per particle to be emitted over the first ~5×10$^{-13}$ s following the pump pulse. Under the assumption of incoherent radiation, the extrapolation of this result to a cubic centimeter of a composite gain medium with a volume fraction of spheroids of $f$=0.25 results in a vacuum energy density of ~5×10$^{-4}$ J/cm$^{-3}$.

The measurement of this emitted energy will be in direct competition with spontaneous emission from the upper level of the dye. The spontaneous emission energy per unit volume can be estimated from equation (23) by using the values $\alpha_s$ and $\xi$ the spontaneous lifetime $\gamma_{sp}^{-1}$ and the duration of the measurement period, taken to be $T_0$=6$\gamma^{-1}$,. When the entire dye bandwidth ($\Delta\omega$) is collected and a quantum efficiency of 100% is assumed, the result is given by:

$$E_s = \frac{6(1-f)\xi \alpha_s \hbar \omega_0}{\sigma_{34}} \left[ \frac{1}{\gamma} \right] \quad (26)$$

Using the values of the parameters, the energy density due to spontaneous emission over the first ~6×10$^{-13}$ s after the pump pulse is estimated to be ~$5.25\times10^{-5}$ J/cm$^3$, approximately an order of magnitude lower than the narrowband vacuum signal. However, if the spontaneous signal is filtered over the same bandwidth ($\delta\omega$), we expect a spontaneous emission per unit volume of ~$6.75\times10^{-6}$ J/cm$^3$, two orders of magnitude less than the vacuum signal. The magnitude of the vacuum signal is of course subject to the choice of the parameter $\xi$ which can be experimentally made to be arbitrarily close to $\xi=1$, resulting in a stronger or weaker emitted vacuum energy relative to the spontaneous emission background.

In addition to the potentially large signal to background ratio predicted for vacuum plasmon effect, it has a significantly different behavior with respect to pump fluence, which is directly proportional to the variable $\xi$. The spontaneous emission signal scales as $\xi$ while the vacuum signal scales as $(\xi-1)^{-2}$. Furthermore, the use of prolate spheroids results in a preferential interaction of vacuum modes with polarizations parallel to the long axis of the structure, resulting in a highly polarized emission relative to depolarized spontaneous emission. Additional signal discrimination is possible by positioning the gain linecenter off of the passive plasmon resonance. This will have a weak effect on the position of the vacuum emission signal and require a higher peak gain for the dye but, will provide a significant spectral shift of emission relative to the peak of the spontaneous emission.

Figure 7:
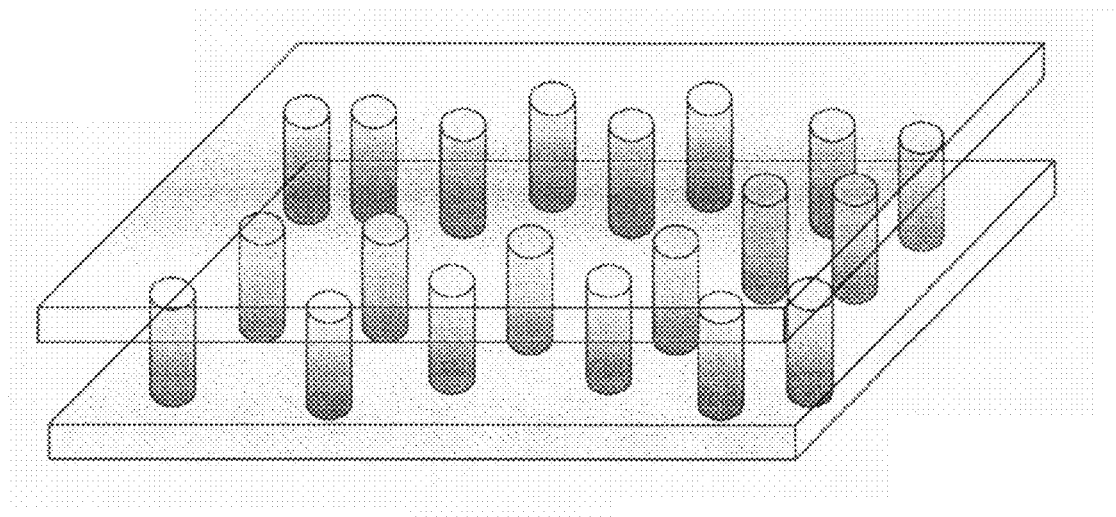
FIG. 7 is a random array of high aspect ratio metallic nanorods with a laser dye or polymeric gain medium in between the rods in accordance with an embodiment of the present invention.

The experimental system for observing this new type of radiation is comprised of commercially available femtosecond lasers and lithographic mask and electro-deposition techniques for the creation of rod structures on various substrates. Turning now to FIG. 7, a random array of high aspect ratio metallic nanorods with a laser dye or polymeric gain medium in between the rods is shown. Such a sample can be excited through the top or bottom plate with highly polarized emission expected in the plane of the plates. The embodiment of FIG. 7 shows the use of a transparent substrate with a surface coverage of rods and a high gain dye as an ideal test structure for observing the predicted emission. For the surface coverage of rods of ~$10^{10}$/cm$^2$, and a spacer of 500 nm, we expect a vacuum signal of ~$1.5\times10^{-7}$ J/cm$^2$ while the spontaneous emission signal in the same bandwidth is ~$2.25\times10^{-10}$ J/cm$^2$. The use of either streak camera or time resolved sum frequency generation methods can be used to measure the emitted energies as a function of time and delay relative to the pump.

While the invention has been described with reference to illustrative embodiments, it will be understood by those skilled in the art that various other changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A structure comprising:
    one or more nano-particles surrounded by an amplifying medium, the one or more nano-particles and the amplifying medium arranged such that a boundary condition is formed at an interface of the one or more nano-particles and the amplifying medium, there being a divergence in the dynamic polarizability of the one or more nano-particles or in the dielectric function of a composite of the nano-particles at a resonance determined by the localized surface plasmon-polariton or phonon-polariton resonance of the one or more nano-particles and at a critical value of gain of the localized surface plasmon-polariton or phonon-polariton resonance.

2. A structure comprising:
    nanoscale structures embedded in an amplifying media, there being a divergence in the optical polarizability of the nanoscale structures, the nanoscale structures and the amplifying media arranged such that a dynamic boundary condition is formed at an interface of the nanoscale structures and the amplifying media, wherein the dynamic boundary condition is coupled to an electromagnetic vacuum or a field.

* * * * *